(12) United States Patent
Pinkerton et al.

(10) Patent No.: US 7,060,501 B2
(45) Date of Patent: Jun. 13, 2006

(54) METHODS FOR SELECTING AND SCREENING FOR PLANT CELLS TRANSFORMED WITH A POLYNUCLEOTIDE ENCODING AN ORGANOPHOSPHATE HYDROLASE

(75) Inventors: T. Scott Pinkerton, College Station, TX (US); John A. Howard, College Station, TX (US); James R. Wild, College Station, TX (US)

(73) Assignee: Applied Biotechnology Institute, College Station, TX (US)

( * ) Notice: Subject to any disclaimer, the term of this patent is extended or adjusted under 35 U.S.C. 154(b) by 116 days.

(21) Appl. No.: 10/727,010

(22) Filed: Dec. 3, 2003

(65) Prior Publication Data

US 2004/0250298 A1    Dec. 9, 2004

Related U.S. Application Data

(60) Provisional application No. 60/430,626, filed on Dec. 3, 2002.

(51) Int. Cl.
*C12N 15/82* (2006.01)
*C12Q 1/34* (2006.01)

(52) U.S. Cl. .......................................... 435/468; 435/18

(58) Field of Classification Search .................... 435/6, 435/468, 18; 800/300
See application file for complete search history.

(56) References Cited

U.S. PATENT DOCUMENTS 6,380,465 B1 *   4/2002   Barrett ...................... 800/300

FOREIGN PATENT DOCUMENTS

WO    WO 99/53037     * 10/1999
WO    WO 01/96543 A2 * 12/2001

OTHER PUBLICATIONS

Phillips et al, Proc. Natl. Acad. Sci. USA 1990, 87:8155-8159.*
Blume et al., "Alteration of β-tubulin in *Nicotiana plumbaginifolia* confers resistance to amiprophos-methyl", Theor. Appl. Genet. 97:464-472 (1998).

* cited by examiner

*Primary Examiner*—David H Kruse
(74) *Attorney, Agent, or Firm*—Patricia A. Sweeney

(57) ABSTRACT

The present invention provides novel methods for determining whether a cell has incorporated a polynucleotide comprising the use of organophosphate hydrolase activity as a marker which has both selectable and screenable properties.

14 Claims, 5 Drawing Sheets

SEQUENCE LISTING

```
<160> NUMBER OF SEQ ID NOS: 2

<210> SEQ ID NO 1
<211> LENGTH: 982
<212> TYPE: DNA
<213> ORGANISM: Artificial Sequence
<220> FEATURE:
<223> OTHER INFORMATION: Sequence originally obtained from
      Flavobacterium sp., Genbank accession number M29593.  Sequence
      translated and back-translated with BACKTRANSLATE (Wisc. GCG, ver.
      9).  Deleterious sequences removed with FINDPATTERN (Wisc. GCG,
      ver. 9).
```

```
-continued

<400> SEQUENCE: 1
cggcccgatc accatctccg aggccggctt caccctcacc cacgagcaca tctgcggctc      60
ctccgccggc ttcctccgcg cctggccgga gttcttcggc tcccgcaagg ccctcgccga     120
gaaggccgtg cgcggcctcc gccgcgcccg cgccgccggc gtgcgcacca tcgtggacgt     180
gtccaccttc gacatcggcc gcgacgtgtc cctcctcgcc gaggtgtccc gcgccgccga     240
cgtgcacatc gtggccgcca ccggcctctg gttcgacccg ccgctctcca tgcgcctccg     300
ctccgtggag gagctcaccc agttcttcct ccgcgagatc cagtacggca tcgaggacac     360
cggcatccgc gccggcatca tcaaggtggc caccaccggc aaggccaccc cgttccagga     420
gctcgtgctc aaggccgccg cccgcgcctc cctcgccacc ggcgtgccgg tgaccaccca     480
caccgccgcc tcccagcgcg acggcgagca gcaggccgcc atcttcgagt ccgagggcct     540
ctccccgtcc cgcgtgtgca tcggccactc cgacgacacc gacgacctct cctacctcac     600
cgccctcgcc gcccgcggct acctcatcgg cctcgaccac atcccgcact ccgccatcgg     660
cctcgaggac aacgcctccg cgtccgccct cctcggcatc cgctcctggc agacccgcgc     720
cctcctcatc aaggccctca tcgaccaggg ctacatgaag cagatcctcg tgtccaacga     780
ctggctcttc ggcttctcct cctacgtgac caacatcatg gacgtgatgg accgcgtgaa     840
cccggacggc atggccttca tcccgctccg cgtgatcccg ttcctccgcg agaagggcgt     900
gccgcaggag accctcgccg gcatcaccgt gaccaacccg gcccgcttcc tctccccgac     960
cctccgcgcc tcctgagtta ac                                              982

<210> SEQ ID NO 2
<211> LENGTH: 100
<212> TYPE: DNA
<213> ORGANISM: Artificial Sequence
<220> FEATURE:
<223> OTHER INFORMATION: barley alpha-amylase signal sequence (BAASS)

<400> SEQUENCE: 2
ccatggccaa caagcacctg agcctctccc tcttcctcgt gctcctcggc ctctccgcct      60
ccctcgccag cggcaccggc gaccgcatca acaccgtgcg                           100
```

METHODS FOR SELECTING AND SCREENING FOR PLANT CELLS TRANSFORMED WITH A POLYNUCLEOTIDE ENCODING AN ORGANOPHOSPHATE HYDROLASE

CROSS-REFERENCE TO RELATED APPLICATIONS

This application claims benefit under 35 U.S.C. § 119(e) of U.S. Provisional Application Ser. No. 60/430,626 filed Dec. 3, 2002, which is herein incorporated by reference in its entirety.

BACKGROUND OF THE INVENTION

1. Field of the Invention

The present invention relates generally to methods for nucleic acid detection. More specifically, embodiments of the invention relate to a polynucleotide that acts as a "marker" for the presence of the same or a different polynucleotide of interest. In such embodiments, methods rely on the use of organophosphate hydrolase activity as a marker which has both selectable and screenable properties.

2. Description of the Related Art

Methods to detect nucleic acids and to detect specific nucleic acids provide a foundation upon which the large and rapidly growing field of molecular biology is built. There is constant need for alternative methods and products. The reasons for selecting one method over another are varied, and include a desire to avoid radioactive materials, the lack of a license to use a technique, the cost or availability of reagents or equipment, the desire to minimize the time spent or the number of steps, the accuracy or sensitivity for a certain application, the ease of analysis, or the ability to automate the process.

The detection of nucleic acids or specific nucleic acids is often a portion of a process rather than an end in itself. There are many applications of the detection of nucleic acids in the art, and new applications are always being developed. The ability to detect and quantify nucleic acids is useful in detecting microorganisms, viruses and biological molecules, and thus affects many fields, including human and veterinary medicine, food processing and environmental testing. Additionally, the detection and/or quantification of specific biomolecules from biological samples (e.g., tissue, sputum, urine, blood, semen, saliva) has applications in forensic science, such as the identification and exclusion of criminal suspects and paternity testing as well as in genetics and medical diagnostics.

However, many attempts have been made to genetically engineer desired traits into genomes by introduction of exogenous genes using genetic engineering techniques. An important aspect of the success achieved in genetic engineering has been the ability to select or screen for transgenic cells. Most of the first successes in genetic engineering relied on utilization of selectable markers for identification of transgenic cells. Markers which have been used for selection of transgenic cells include, for example, genes that confer resistance to antibiotics and other-toxins, including, for example, ampicillin, neomycin, puromycin, methotrexate or tetracycline, those that complement auxotrophic deficiencies, or those supply critical nutrients not available from complex media. Other selectable markers include the dihydrofolate reductase gene, which confers resistance to methotrexate, and thymidine kinase, or genes conferring resistance to G418 or hygromycin. Commonly used selectable markers for plant transformation include a neomycin phosphotransferase gene (Potrykus et al., *Mol. Gen. Genet.* 199:183 (1985)), which provides resistance to kanamycin, paromomycin and G418; a bar gene which codes for bialaphos or phosphinothricine resistance (U.S. Pat. No. 5,550,318); a mutant aroA gene which encodes an altered EPSP synthase protein conferring glyphosate resistance (Hinchee et al., *Bio/Technology* 6:915–22 (1988)); a nitrilase gene such as bxn from *Klebsiella ozaenae* which confers resistance to bromoxynil (Stalker et al., *J. Biol. Chem.* 263:6310–14 (1988)); a mutant acetolactate synthase gene (ALS) which confers resistance to imidazolinone, sulfonylurea or other ALS inhibiting chemicals (European Patent Application No. 154,204, 1985); a methotrexate resistant DHFR gene (Thillet et al., *J. Biol. Chem.* 263:12500–08 (1988)); a dalapon dehalogenase gene that confers resistance to the herbicide dalapon; and a mutated anthranilate synthase gene that confers resistance to 5-methyl tryptophan.

More recently, interest has increased in utilization of screenable or scorable markers. A screenable or scorable marker is a gene that codes for a protein whose activity is easily detected, allowing cells expressing such a marker to be readily identified. Such screenable markers include a β-glucuronidase, or uidA gene (GUS), which encodes an enzyme for which various chromogenic substrates are known; chloramphenicol acetyl transferase; alkaline phosphatase; a R-locus gene, which encodes a product that regulates the production of anthocyanin pigments (red color) in plant tissues (Dellaporta et al., in CHROMOSOME STRUCTURE AND FUNCTION, Kluwer Academic Publishers, Appels and Gustafson eds., pp. 263–282 (1988)); a p-lactamase gene (Sutcliffe, *Proc. Nat'l. Acad. Sci. U.S.A.* 75:3737 (1978)), which encodes an enzyme for which various chromogenic substrates are known (e.g., PADAC, a chromogenic cephalosporin); a xylE gene (Zukowsky et al., *Proc. Nat'l. Acad. Sci. U.S.A.* 80:1101 (1983)), which encodes a catechol dioxygenase that can convert chromogenic catechols; an a-amylase gene (Ikuta et al., *Biotech.* 8:241 (1990)); a tyrosinase gene (Katz et al., *J. Gen. Microbiol.* 129:2703 (1983)), which encodes an enzyme capable of oxidizing tyrosine to DOPA and dopaquinone, which in turn condenses to form the easily detectable compound melanin; a β-galactosidase gene, which encodes an enzyme for which there are chromogenic substrates; a lux gene, which encodes a luciferase, the presence of which may be detected using, for example, X-ray film, scintillation counting, fluorescent spectrophotometry, low-light video cameras, photon counting cameras or multiwell luminometry; and a green fluorescent protein (GFP) gene (Sheen et al., *Plant J.* 8(5):777–84 (1995)).

Despite the abundance of selectable and screenable markers for genetic engineering, there are very few, if any, markers which have both selectable and screenable properties. It would be beneficial if another marker were available for detecting the presence of a polynucleotide. It is therefore an object of the present invention to provide methods for determining whether a cell has incorporated a polynucleotide using a marker which has selectable and/or screenable properties.

SUMMARY OF THE INVENTION

The present invention provides novel methods for determining whether a cell has incorporated a polynucleotide. Such a method utilizes organophosphate hydrolase activity as a marker, which has both selectable and screenable properties to detect the presence or absence of the polynucleotide in the cell.

According to one aspect of the invention, there is provided a method for determining whether a cell has incorporated and expresses a polynucleotide comprising introducing to a cell a construct comprising a polynucleotide encoding an enzyme having organophosphate hydrolase activity; contacting the cell with an organophosphate such that if the cell does not contain the construct and an organophosphate hydrolase is not thereby produced, the cell growth is inhibited, thereby determining whether the cell has incorporated a polynucleotide.

According to another aspect of the invention, there is provided a method for determining whether a cell has incorporated and expresses a polynucleotide comprising introducing to a cell a construct comprising a polynucleotide encoding an enzyme having organophosphate hydrolase activity; contacting the cell with an organophosphate such that if the cell contains the construct and an organophosphate hydrolase is thereby expressed, the organophosphate hydrolase hydrolyzes the organophosphate; and detecting the hydrolysis, thereby determining whether the cell has incorporated a polynucleotide.

According to yet another aspect of the invention, there is provided a method for determining whether a cell has incorporated a first polynucleotide comprising introducing to a cell a construct comprising a first polynucleotide and a second polynucleotide, wherein the second polynucleotide encodes an enzyme having organophosphate hydrolase activity; contacting the cell with an organophosphate such that if the cell does not contain the construct and an organophosphate hydrolase is not thereby produced, the cell growth is inhibited, thereby determining whether the cell has incorporated a first polynucleotide.

According to yet another aspect of the invention, there is provided a method for determining whether a cell has incorporated a first polynucleotide comprising introducing to a cell a construct comprising a first polynucleotide and a second polynucleotide, wherein the second polynucleotide encodes an enzyme having organophosphate hydrolase activity; contacting the cell with an organophosphate such that if the cell contains the construct and an organophosphate hydrolase is thereby expressed, the organophosphate hydrolase hydrolyzes the organophosphate; and detecting the hydrolysis, thereby determining whether the cell has incorporated a first polynucleotide.

BRIEF DESCRIPTION OF THE FIGURES

FIG. 5A shows the seedlings from the control group; FIG. 5B shows the seedlings following exposure to 0.35 ml of Bensumec 4LF; and FIG. 5C shows the seedlings following exposure to 3.5 ml of Bensumec 4LF.

DETAILED DESCRIPTION OF THE INVENTION

The present invention provides novel methods for determining whether a cell has incorporated a polynucleotide. Such methods utilize an enzyme that has organophosphate hydrolase activity. Such hydrolysis can be detected and a polynucleotide encoding such an enzyme can be used as a scorable and/or selectable marker to determine whether the polynucleotide has been incorporated into a cell.

As used herein, the term "organophosphate hydrolase activity" is intended to refer to that activity which results in the hydrolysis of an organophosphate.

Many cells contain very low levels of endogenous organophosphate hydrolase activity that would not interfere with the ability of the user of the inventive methods to determine if a foreign polynucleotide was indeed incorporated into the cell, and the inventors do not wish to be limited to the use of those cells which contain no organophosphate hydrolase activity. Such measurements of enzyme activity are readily known to those of skill in this art.

Hydrolysis of Organophosphates by Organophosphate Hydrolase

Figure 1:
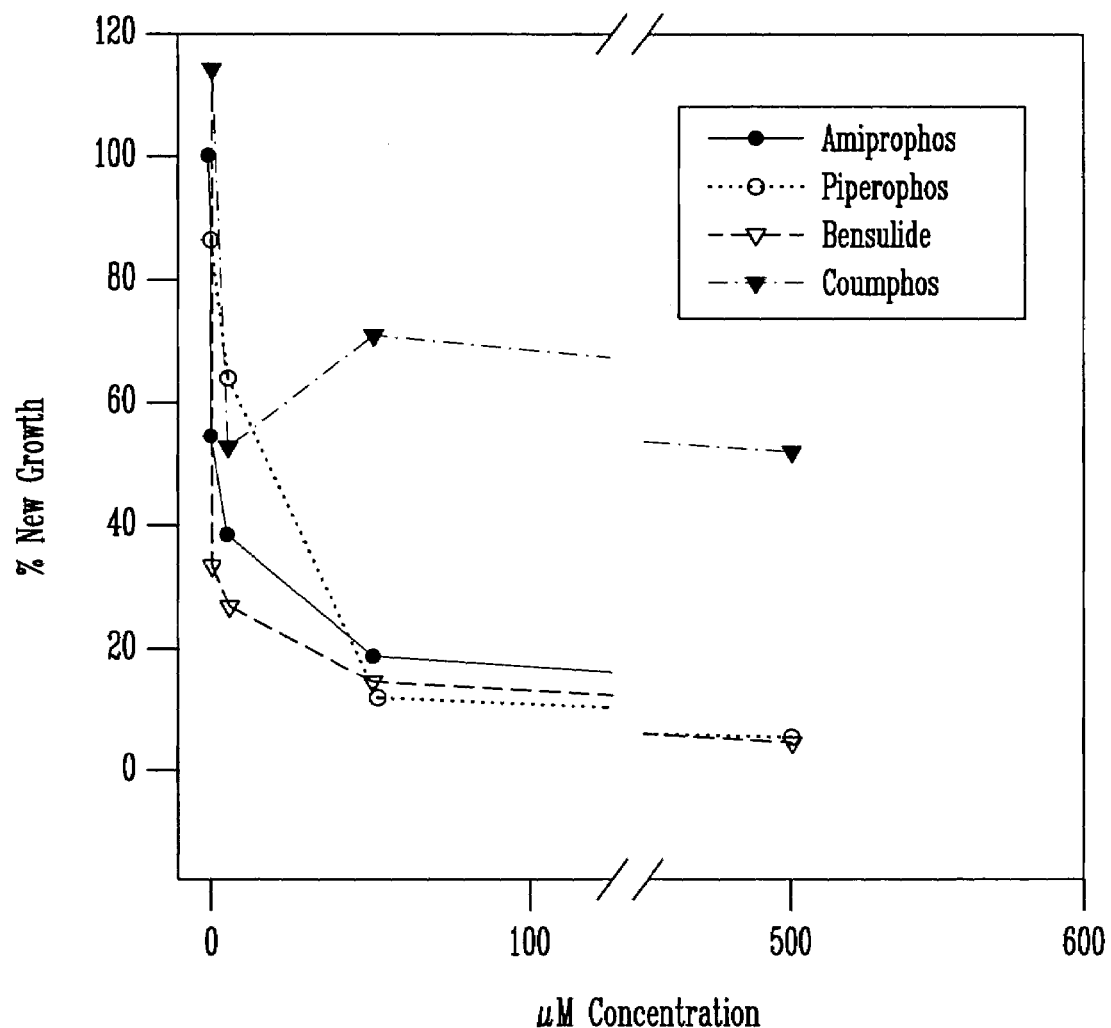
FIG. 1 is a graph showing the effect of the organophosphates amiprophos-methyl, piperophos, bensulide, and coumaphos on maize callus growth. Control callus growth was 824% of initial mass at three weeks.

Synthetic organophosphates are used extensively as agricultural and domestic pesticides, including insecticides, fungicides, and herbicides. FIG. 1 demonstrates the inhibitory effect that the organophosphate herbicides amiprophos-methyl, piperophos, and bensulide, and the organophosphate insecticide coumaphos, has on new growth from maize callus. Naturally occurring bacterial isolates capable of metabolizing this class of compounds have received considerable attention since they provide the possibility of both environmental and in situ detoxification. *Pseudomonas putida* MG, *Pseudomonas diminuta*, and *Flavobacterium* spp. possess the ability to degrade an extremely broad spectrum of organophosphate phosphotriesters as well as thiol esters. McDaniel et al., *J. Bacteriology* 170(5):2306–11 (1988).

Figure 2:
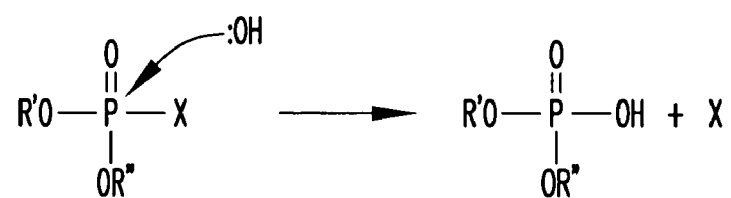
FIG. 2 shows the general scheme of hydrolysis of an organophosphate by organophosphate hydrolase ("X" is O, F, C, or S; "R" is any alkyl group).

Organophosphate hydrolase (EC 3.1.8.1) is a broad spectrum enzyme that is capable of detoxifying organophosphates by creating various phosphoryl bonds (P—O, P—F, P—CN, and P—S) between the phosphorous center and varying electrophilic leaving groups. Dave et al., *Chem.- Biol. Interact.* 87:55–68 (1993). FIG. 2 demonstrates the general scheme of hydrolysis of an organophosphate by organophosphate hydrolase. This enzyme is often identified by other names such as paraoxonase; A-esterase; aryltriphosphatase; organophosphate esterase; esterase B1; esterase E4; paraoxon esterase; pirimiphos-methyloxon esterase; OPA anhydrase; organophosphorus hydrolase; phosphotriesterase; paraoxon hydrolase; OPH; organophosphorus acid anhydrase; DFPase; parathion hydrolase; parathion aryl esterase; somanase; and sarinase. The hydrolytic reaction rates with several phosphotriesterases appear to be limited by diffusion to the active center of the enzyme. Caldwell et al., *Biochemistry* 30:7438–44 (1991). Organophosphate hydrolase is the only enzyme which has been shown to be able to hydrolyze the P—S bond of various phosphorothioate pesticides. The toxicity of hydrolyzed products has been shown to be significantly reduced as indicated by the loss of inhibition of acetylcholinesterase activity and by decreased neurotoxic response in animals. Kolakowski et al., *Biocat. Biotrans.* 15:297–312 (1997). Phosphorothioate pesticides such as acephate, azinophos-methyl, demeton-S-methyl, malathion, and phosalone have been shown to be hydrolyzed by organophosphate hydrolase. The hydrolysis of these pesticides has a first order dependency on the amount of enzyme used and the reaction time. Organophosphate hydrolase hydrolyzes acephate, azinophos-methyl, demeton-S-methyl and phosalone at rates which are thousands of times greater than that which occurs during strong alkaline hydrolysis. In contrast, the enzyme possesses poor capability for malathion hydrolysis, although still significantly better than non-enzymatic hydrolysis under similar conditions. When compared to the hydrolysis of P—O bond phosphotriester substrates and P—F bond phosphofluoridate substrates, the thioesters (P—S bond esters) hydrolysis was much slower in general. See Kolakowski et al., supra.

Other organophosphates that have been shown or have the potential to be hydrolyzed by organophosphate hydrolase include, but are not limited to, the microtubule assembly inhibitor amiprophos-methyl, the cell division inhibitor piperophos, the lipid synthesis inhibitor bensulide, paraoxon, DFP, coumaphos, soman, and VX.

Hydrolysis of Amiprophos-Methyl by Organophosphate Hydrolase

Figure 3:
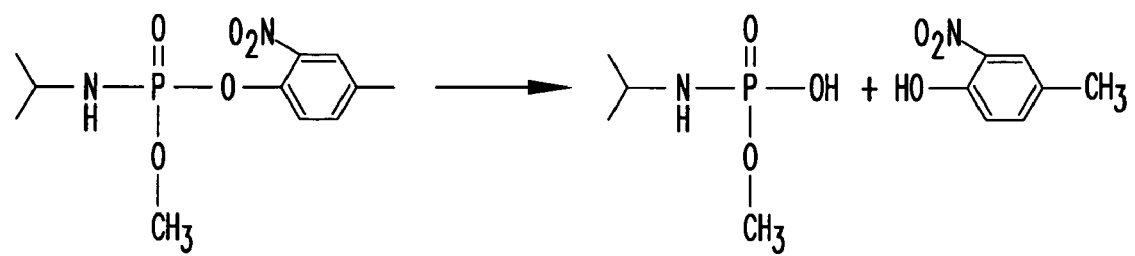
FIG. 3 shows the hydrolysis of amiprophos-methyl by organophosphate hydrolase. A product of this reaction is 4-methyl-2-nitrophenol.
Figure 4:
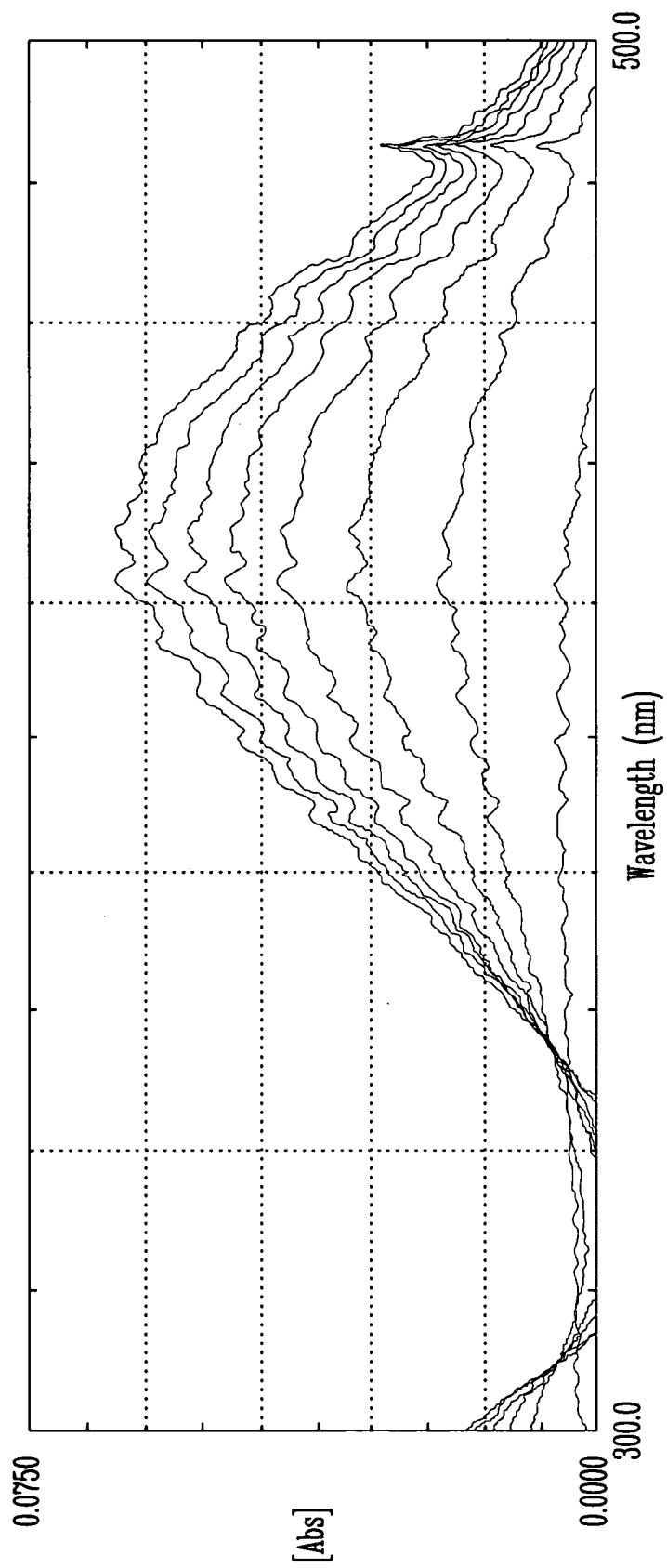
FIG. 4 is a spectrometer wavelength graph (scans taken every 30 seconds) in which cleavage of 0.5 mM of amiprophos-methyl by 2 µg of organophosphate hydrolase results in the absorbance of light. A product of the reaction, 4-methyl-2-nitrophenol, is yellow in color ($\epsilon$=1800 $M^{-1}cm^{-1}$ at 435 nm).

FIG. 3 demonstrates the scheme of hydrolysis of the organophosphate amiprophos-methyl by organophosphate hydrolase. A product of this hydrolytic reaction is the compound 4-methyl-2-nitrophenol. This compound is yellow in color ($\epsilon=1800$ $M^{-1}cm^{-1}$ at 435 nm), as demonstrated by the spectrometer wavelength graph in FIG. 4.

Polynucleotide Encoding Enzyme Having Organophosphate Hydrolase Activity

A polynucleotide encoding an enzyme having organophosphate hydrolase activity is preferably obtained from *Flavobacterium* sp. (Genbank accession numbers M29593 or M22863), but can also be obtained from other sources, including, but not limited to, *Pseudomonas diminuta* (Genbank no. M20392) and *Agrobacterium tumefaciens* (Genbank no. AY043245).

Polynucleotides encoding an enzyme having organophosphate hydrolase or organophosphate hydrolase-like activity, such as paraoxonase (PON) and organophosphate acid anhydrase, are also contemplated. PON hydrolyzes P—C, P—O, P—F, and P—CN bonds, but not P—S bonds, and has been isolated from *Homo sapiens* (human; Genbank no. NMA_000446), *Mus musculus* (mouse; Genbank no. NM_008896), *Gallus gallus* (chicken; Genbank no. BM427017), *Orycolagus cuniculus* (rabbit; Genbank no. AF220944), *Danio rerio* (zebra fish; Genbank no. B1709981), *Xenopus laevis* (frog; Genbank no. BE506006), *Rattus norvegicus* (rat; Genbank no. AA817964), and *Melagris gallopavo* (prairie chicken; Genbank no. L47572). Organophosphate acid anyhdrase hydrolyzes P—O, P—F, and P—CN bonds, and has been isolated from *Mycobacterium* sp. (Genbank no. M91040) and *Nocardia* sp. (Genbank no. JC1378).

Polynucleotide Constructs, Vectors, and Cells

A construct comprising a polynucleotide encoding an enzyme having orgnanophosphate hydrolase activity is one that permits expression of the polynucleotide. Such a construct typically further comprises a transcription unit of a promoter operably linked to the polynucleotide which is functional in a cell, and a termination or polyadenylation signal. The construct can further comprise additional polynucleotides that do not encode an enzyme having organophosphate hydrolase activity, however are expressed in the cell.

The polynucleotide construct typically forms part of a transformation vector. Generally, such vectors comprise cis-acting control regions effective for expression in a cell operatively linked to the polynucleotide to be expressed. Appropriate trans-acting factors either are supplied by the cell, supplied by a complementing vector or supplied by the vector itself upon introduction to the cell.

A great variety of expression vectors can be used to express a polynucleotide encoding an enzyme having organophosphate hydrolase activity as well as other polynucleotides. Such vectors include chromosomal, episomal and virus-derived vectors, e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express polynucleotides to express a polypeptide in a cell can be used for expression in this regard.

A polynucleotide encoding an enzyme having organophosphate hydrolase activity contained in the vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters, and promoters of retroviral LTRs, to name just a few of the well-known promoters. For maize expression vectors, promoters include, for example, the ubiquitin and globulin promoters. In general, expression vectors will contain sites for transcription, initiation and termination, and, in the transcribed region, a ribosome binding site for translation. The coding portion of the mature transcripts expressed by the vectors will include a translation initiating AUG at the beginning and a termination codon (UAA, UGA or UAG) appropriately positioned at the end of the polypeptide to be translated.

In addition, the vectors can contain control regions that regulate as well as engender expression. Generally, such regions will operate by controlling transcription, such as repressor binding sites and enhancers and leaders, among others.

The vector comprising a construct comprising a polynucleotide encoding an enzyme having organophosphate hydrolase activity, as well as an appropriate promoter, and other appropriate control sequences, and optional additional polynucleotides, can be introduced to an appropriate cell using a variety of well known techniques suitable to expression therein of a polynucleotide encoding an enzyme having organophosphate hydrolase activity. Representative examples of appropriate cells include bacterial cells, such as *E. coli, Streptomyces* and *Salmonella typhimurium* cells; fungal cells, such as yeast cells; insect cells such as *Droso-*

*phila* S2 and *Spodoptera* Sf9 cells; animal cells such as CHO, COS and Bowes melanoma cells; and plant cells, such as maize cells. Cells for a great variety of expression constructs and vectors are well known, and those of skill will be enabled by the present disclosure readily to select a cell for expressing a polynucleotide encoding an enzyme having organophosphate hydrolase activity in accordance with the invention. Preferably, the cell is one that does not naturally contain an enzyme having significant organophosphate hydrolase activity.

Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors available to those of skill in the art.

Selection of appropriate constructs, vectors, and promoters for expression in a cell is a well known procedure, and the requisite techniques for expression construct/vector construction, introduction of a construct, or vector comprising a construct, to a cell and expression in the cell are routine skills in the art.

Transformation

Once a polynucleotide encoding an enzyme having organophosphate hydrolase activity is obtained, it is introduced to an appropriate cell. Preferably, such introduction is accomplished through the use of a vector. The vector can be, for example, a plasmid vector, a single or double-stranded phage vector, or a single or double-stranded RNA or DNA viral vector. Such vectors can be introduced to cells as polynucleotides, preferably DNA, by well-known techniques for introducing DNA and RNA to cells. Viral vectors can be replication competent or replication defective. In the latter case viral propagation generally will occur only in complementing cells.

Introduction of a vector comprising a polynucleotide encoding an enzyme having organophosphate hydrolase activity to a cell can be effected by calcium phosphate transfection, DEAE-dextran mediated transfection, cationic lipid-mediated transfection, electroporation, transduction, infection or other methods. Such methods are described in many standard laboratory manuals, such as Davis et al., BASIC METHODS IN MOLECULAR BIOLOGY, Appleton & Lang, Norwalk, Conn. (1986).

For plant cells, various methods are known in the art to accomplish genetic transformation. Among these methods are *Agrobacterium* species transformation and direct gene transfer.

*Agrobacterium tumefaciens* is the etiologic agent of crown gall. The wild type form of *Agrobacterium tumefaciens* carries the Ti (tumor-inducing) plasmid that directs the production of tumorigenic crown gall growth on the host plants. The crown gall is produced following the transfer of the tumor inducing T-DNA region from the Ti plasmid into the genome of an infected plant. This DNA fragment encodes genes for auxin and cytokinin biosynthesis, and it is these hormones in high concentration that promote growth of undifferentiated cells in the crown gall. Transfer of the T-DNA to the plant genome requires that the Ti plasmid-encoded virulence genes as well as the T-DNA borders, a set of direct DNA repeats that delineate the region to be transferred. The tumor inducing genes can be removed from Ti plasmid vectors, disarming the pathogenic nature of the system, without affecting the transfer of DNA fragments between the T-DNA borders. Therefore, the tumor inducing genes are generally replaced with a gene encoding resistance to kanamycin, or some other gene, to allow for selection of transformants, and a gene encoding the desired trait. The *Agrobacterium* containing the engineered plasmid is co-cultivated with cultured plant cells or wounded tissue. The de-differentiated plant cells are then propagated on selective media, and a transgenic plant is subsequently regenerated from the transformed cells by altering the levels of auxin and cytokinin in the growth medium.

Current protocols for *Agrobacterium* mediated transformation often employ binary vector systems, which divide the Ti plasmid into two components, a shuttle vector and a helper plasmid. The helper plasmid, which is permanently placed in the *Agrobacterium* host, carries the virulence genes. However, a much smaller shuttle vector contains T-DNA borders, a broad-host range bacterial origin of replication, antibiotic resistance markers, and a multiple cloning site for incorporation of the foreign gene. In the alternative, a similar strategy employs cointegrating Ti plasmid vectors, whereby an intermediate plasmid containing antibiotic resistance, the gene to be transferred and one T-DNA border are used to transform *A. tumefaciens* containing a disarmed Ti plasmid possessing the virulence genes and one T-DNA border. The two plasmids homologously recombined in vivo at the T-DNA borders placing the antibiotic resistance gene and the gene of interest between two T-DNA borders, one from each plasmid. The genes are then transferred into plant tissue upon co-cultivation.

The *Agrobacterium* system has been well studied and has further been developed into a system which permits routine transformation of a variety of plant tissues. See, e.g., Schell et al., *Bio/Technology* 1:175 (1983); Chilton, *Scientific American* 248:50 (1983). Some of the tissues transformed utilizing *Agrobacterium* include tobacco, Barton et al., *Cell* 32:1033 (1983); tomato, Fillatti et al., *Bio/Technology* 5:726 (1987); sunflower, Everett et al., *Bio/Technology* 5:1201 (1987); cotton, Umbeck et al., *Bio/Technology* 5:263 (1987); canola, Pua et al., *Bio/Technology* 5:815 (1987); potato, Facciotti et al., *Bio/Technology* 3:241 (1985); poplar, Pythoud et al., *Bio/Technology* 5:1323 (1987); and soybean, Hinchee et al., *Bio/Technology* 6:915 (1988).

In a preferred method of *Agrobacterium* transformation, the *Agrobacterium* transformation methods described in U.S. Pat. No. 5,591,616 are generally followed, with modifications that the inventors have found improve the number of transformants obtained. This method uses the A188 variety of maize that produces Type I callus in culture. In one preferred embodiment the HiII maize line is used which initiates Type II embryogenic callus in culture. While selection on phosphinothricin is recommended when using the bar or PAT gene for selection, another preferred embodiment provides for use of bialaphos instead.

The bacterial strain used in this protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* specific replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA 101, selecting for spectinomycin resistance. The plasmid is isolated to assure that the EHA101 contains the plasmid.

Further, the protocol as described provides for growing a fresh culture of the *Agrobacterium* on plates, scraping the bacteria from the plates, and resuspending in the co-culture medium, as stated in U.S. Pat. No. 5,591,616 for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose, and 36 g glucose, all at a pH of 5.8. In a further preferred method, the bacteria are grown overnight in a 1 ml culture, and then a fresh 10 ml culture re-inoculated the next day when transformation is to occur. The bacteria grow into log phase, and are harvested at a density of no more than $OD_{600}=0.5$ and is preferably between 0.2 and 0.5. The bacteria are then centrifuged to remove the media and resuspended in the co-culture medium. Since HiII is used, medium preferred for HiII is used. This medium is described in considerable detail by Armstrong et al., *Planta* 154:207–14 (1985). The resuspension medium is the same as that described above. All further HiII media are as described in Armstrong et al., supra. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

Another vector for biological plant transformation is *Agrobacterium rhizogenes*. *A. rhizogenes*, which incite root formation in many dicotyledonous plant species, carries the R1 (root-inducing) plasmid which functions in a manner analogous to the Ti plasmid of *A. tumefaciens*. Transformation using A. rhizogenes has also been successfully utilized to transform plants, for example, alfalfa, Sukhapinda et al., *Plant Mol. Biol.* 8:209 (1987); *Solanum nigrum* L., Wei et al., *Plant Cell Reports* 5:93 (1986); and, poplar, Pythoud et al., supra.

Several direct gene transfer procedures have also been developed to transform plant cells. In the direct transformation of protoplasts, the uptake of exogenous genetic material into a protoplast can be enhanced by use of a chemical agent or electric field. The exogenous material can then be integrated into the nuclear genome. Microprojectile bombardment, electroporation in addition to several other direct transformation methods exist and are known to those of skill in the art.

Electroporation is another effective means of introducing foreign DNA to plant cells. Saul et al., "Direct DNA Transfer to Protoplasts With and Without Electroporation," PLANT MOLECULAR BIOLOGY MANUAL, vol. A1, Kluwer Academic Publishers, Dordrecht, The Netherlands, Gelvin and Schilperoort eds., p. 1 (1988). Since any DNA fragment can be delivered to the cell, this technique has the advantage of allowing assimilation of a gene without having to clone the DNA into a host vector such as *A. tumefaciens*.

Another technique for delivering DNA to intact plant tissue or protoplasts is biollistic projection or microprojectile bombardment. Tomes et al., *Plant Mol. Biol.* 14:21 (1990); Svab et al., *Proc. Nat'l. Acad. Sci. U.S.A.* 87:8526–30 (1990). With this technique, microprojectile particles (e.g., 1.2 micrometer gold or Tungsten beads) coated with DNA are accelerated at high speeds into plant tissue. This approach has the distinct advantage of being applicable to any intact plant tissue or region of the plant and has been used to transform organellar DNA. Svab et al., supra; Boynton et al., *Science* 240:534 (1988). This technique is especially useful for plants that are otherwise recalcitrant with respect to transformation and/or regeneration. For instance, biollistic methods have been successfully used to produce transgenic monocot cereal plants. Potrykus (1991), supra; Wu et al., "Transformation and Regeneration of Important Crop Plants; Rice is the Model System for Monocots," in GENE MANIPULATION AND PLANT IMPROVEMENT, vol. 2, Gustafson, J. P., ed., Quantum Press, New York, p. 251 (1990); Gordon-Kamm et al., *Plant Cell* 2:603 (1990).

DNA viruses have been used as gene vectors. Both Cauliflower Mosaic Virus (CaMV) and the closely related Figwort Virus are circular duplex DNA viruses which replicate via transcription of a full-length (35S) genomic RNA intermediate. A cauliflower mosaic virus carrying a modified bacterial methotrexate-resistance gene was used to infect a plant, whereby the foreign gene was systemically spread in the plant. Brisson et al. *Nature* 310:511 (1984); Brisson et al., METHODS FOR PLANT MOLECULAR BIOLOGY, Academic Press, San Diego, Weissbach and Weissbach eds., p. 437 (1988). The strong promoter responsible for the genomic replication of the CaMV virus (the 35S promoter) has been extensively exploited for the expression of heterologous genes in plants. Other advantages of this system are the ease of infection, systemically spread within the plant, and multiple copies of the gene per cell.

Exogenous DNA can be introduced to cells or protoplasts by microinjection. Microinjection is a method where a solution of plasmid DNA is injected directly into the cell with a finely pulled glass needle. Alfalfa protoplasts have been transformed utilizing this method with a variety of plasmids. Reich et al., *Bio/Technology* 4:1001 (1986).

In liposome fusion, protoplasts and liposomes carrying the foreign gene of interest are brought together. As membranes merge, the foreign gene is transferred to the protoplast. Deshayes et al., *EMBO J.* 4:2731 (1985).

A form of chemical mediated transformation utilizes polyethylene glycol (PEG) and has been carried out in *N. tabacum* a dicot, and *Lolium multiflorum*, a monocot. It is a chemical procedure of direct gene transfer based on synergistic interaction between $Mg^{2+}$, PEG, and possibly $Ca^{2+}$. Negrutiu et al., *Plant Mol. Biol.* 8:363 (1987).

Detection of Hydrolysis of Organophosphate

Detection of the hydrolysis of an organophosphate by an enzyme having organophosphate hydrolase activity will depend upon the specific organophosphate being subjected to hydrolysis. For example, hydrolytic reactions may proceed with the absorbance of light (i.e., hydrolysis of amiprophos-methyl), which can be detected by spectrophotometry. Additionally, hydrolytic reactions may result in the production of compounds capable of emitting light, for example, by fluorescence or phosphorescence (i.e., hydrolysis of coumaphos results in the production of a fluorescent compound). Such methods are well known to those of skill in the art. By way of illustration only, OPH activity, for example, can be analyzed by the hydrolysis of paraoxon. Cleavage of paraoxon yields p-Nitrophenol, which is measured spectrophotometrically at 400 nm. So, OPH activity can be assayed in 1 ml plastic cuvettes by observing the hydrolysis of Paraoxon to p-Nitrophenol at 400 nm. Units of enzyme are determined using the extinction coefficient of p-Nitrophenol ($17\ mM^{-1}\ cm^{-1}$).

In the foregoing discussion, a number of citations from professional journals and patents are included for reference. All such citations are hereby incorporated in their entirety by reference.

EXAMPLE 1

Polynucleotide Encoding Enzyme Having Organophosphate Hydrolase Activity

A polynucleotide encoding an enzyme having organophosphate hydrolase activity was obtained from *Flavobacterium* sp. (Genbank accession number M29593). The sequence was translated into a protein sequence and then back translated into a DNA sequence using a maize codon usage table with the BACKTRANSLATE program of the GCG Wisconsin package (Wisconsin Package, version 9, Genetics Computer Group (GCG), Madison, Wis.) and then searched for putative deleterious sequences using the FIND-PATTERN program of the GCG Wisconsin package. Alternative codons were chosen to eliminate the deleterious mRNA signals in the coding sequence and to add convenient enzyme restriction sites to facilitate downstream cloning. Codons that reflected less than 20% usage were avoided. The completed sequence was analyzed for unique restriction sites with the Vector NTI program. Five roughly equidistant sites were chosen for the construction of the polynucleotide encoding the enzyme having organophosphate hydrolase activity. Oligonucleotides were ordered in 50 bp lengths with 25 bp overhangs. These were annealed and amplified by PCR. Amplified products were trapped in a vector and transformed into competent cells. Colonies were analyzed by restriction analysis and by DNA sequencing. Correct clones were then subcloned together in the vector. After the complete sequence (SEQ ID NO:1) was assembled, a barley α-amylase signal sequence (BAASS) (SEQ ID NO:2) was added to ensure high expression in plants, and it was cloned into a maize expression vector under the direction of the ubiquitin promoter and the pinII terminator.

EXAMPLE 2

Transformation

A maize expression vector containing the ubiquitin promoter, the BAASS (SEQ ID NO:2), the polynucleotide encoding an enzyme having organophosphate hydrolase activity (SEQ ID NO:1), and the pinII terminator was transferred to *Agrobacterium* by the method described in U.S. Pat. No. 5,591,616, with modifications that improve the number of transformants obtained. As previously described, this method uses the A188 variety of maize that produces Type I callus in culture. In one preferred embodiment the HiII maize line is used which initiates Type II embryogenic callus in culture. While selection on phosphinothricin is recommended when using the bar or PAT gene for selection, another preferred embodiment provides for use of bialaphos instead.

The bacterial strain used in this protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* specific replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA 101, selecting for spectinomycin resistance. The plasmid is isolated to assure that the EHA101 contains the plasmid.

Further, the protocol as described provides for growing a fresh culture of the *Agrobacterium* on plates, scraping the bacteria from the plates, and resuspending in the co-culture medium, as stated in U.S. Pat. No. 5,591,616 for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose, and 36 g glucose, all at a pH of 5.8. In a further preferred method, the bacteria are grown overnight in a 1 ml culture, and then a fresh 10 ml culture re-inoculated the next day when transformation is to occur. The bacteria grow into log phase, and are harvested at a density of no more than $OD_{600}=0.5$ and is preferably between 0.2 and 0.5. The bacteria are then centrifuged to remove the media and resuspended in the co-culture medium. Since HiII is used, medium preferred for HiII is used. This medium is described in considerable detail by Armstrong et al., *Planta* 154:207–14 (1985). The resuspension medium is the same as that described above. All further HiII media are as described in Armstrong et al., supra. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

EXAMPLE 3

Maize Plant Regeneration from Type II Callus

Regeneration of plants from Type II callus is based upon allowing the embryoids on the surface of the Type II callus to mature and germinate. See Freeling & Walbot, *The Maize Handbook* (1994) at pp. 673–674. The callus are first collected and weighed in petri plates. 1–2 grams fresh weight of soft, friable Type II callus containing numerous embryoids are evenly distributed over the surface of a 100×15 mm petri plate which contains 25 ml of regeneration medium. Regeneration medium consists of Murashige and Skoog (MS) basal salts, modified White's vitamins (0.2 g/l glycine, and 0.5 g/l of each of thiamine-HCl, pyridoxine-HCl, and nicotinic acid), supplemented with 6% sucrose, 0.1 g/l myo-inositol, and 0.8% Bacto-agar (6SMS0D). The plates are then wrapped with Parafilm and placed in the dark. After one week, the plates are moved to a lighted growth chamber with a 16-hour (75 μE m$^{-2}$sec$^{-1}$) and an 8-hour dark photo period. Three weeks after plating the Type II callus to the 6SMS0D, the plate is examined for shoot formation from the calli. The calli and the shoot are then transferred to fresh Bacto-agar plates for another two weeks. The callus without shoots can be left on the Bacto-agar for a longer period if the callus is slow in embryo development. Upon distinct formation of a shoot and root (some may be ready for transfer after the first three weeks on regeneration medium), the newly developed green plantlets are transferred to Magenta GA-7 (Magenta Corp., Chicago, Ill.) containers with 60 ml of 3SMSOD medium solidified with 0.6% Bacto-agar. When the plant has developed a strong root system (10–15 days after transfer into Magenta boxes), the plant is gently removed from the agar, the remaining agar is washed from the roots and shoot, and the plant is carefully transplanted into a 4-inch pot containing moist soil. The pots can then be placed in a high humidity chamber and, over a period of ten days, the humidity can be slowly reduced to approximately that of the greenhouse. Once plants are adapted to a lower humidity, they may be removed from the greenhouse and treated like seedlings.

EXAMPLE 4

Use of Organophosphate Hydrolase as Selectable Marker in Plants

Figure 5A:
FIGS. 5A–C demonstrate the comparative effect of the organophosphate bensulide on maize seedlings that have been transformed with a polynucleotide encoding an enzyme having organophosphate hydrolase activity ("OPA0403-2") and maize seedlings that have not been so transformed ("elite line/HiII Cross").
Figure 5B:
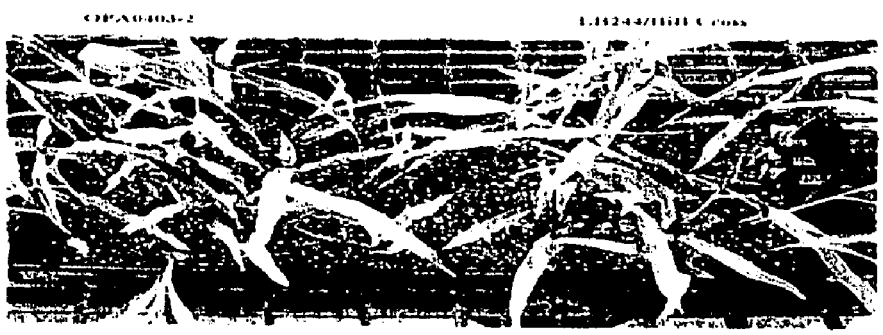
Figure 5C:

Transformed and non-transformed seedlings were sprayed with 0.35 ml and 3.5 ml of Bensumec 4LF (PBI/Gordon Corp., Kansas City, Mo.), the active ingredient of which is the organophosphate bensulide, and examined for germination. FIGS. 5A–C show, respectively, a control group of organophosphate hydrolase-transformed ("OPA0403-2") and non-transformed ("elite line/HiII Cross") seedlings that were not subjected to bensulide treatment; transformed and non-transformed seedlings that were subjected to 0.35 ml of Bensumec 4LF; and transformed and non-transformed seedlings that were subjected to 3.5 ml of Bensumec 4LF. As demonstrated by FIG. 5B, the transformed seedlings subjected to 0.35 ml of Bensumec 4LF exhibited greater resistance to the organophosphate than the non-transformed seedlings. This difference was even more apparent when the transformed and non-transformed seedlings were subjected to 3.5 ml of Bensumec 4LF, where, as shown in FIG. 5C, nearly all of the non-transformed seedlings were killed, while the transformed seedlings were largely unaffected.

EXAMPLE 5

Use of Organophosphate Hydrolase as Screenable Marker in Plants

Two standard, 100×25 mm plant tissue culture plates were prepared, each plate containing 35 ml of 5630 medium. A one-liter solution of 5630 medium (pH 5.6 to 5.8) consists of N6 salts (4 g), Eriksson's vitamins (1 ml of 1000× stock), thiamine-HCl (1 ml of 0.5 mg/ml stock), L-proline (0.7 g), sucrose (20 g), MES buffer (0.5 g), 2,4-D (1.5 ml of 1 mg/ml stock), 8 g agar, bialophos (1 ml of 1.6 mg/ml stock), silver nitrate (1 ml of 0.85 mg/ml stock), and carbenicillin (1 ml of 100 mg/ml stock).

Following plate preparation, 3 ml of a 1 mg/ml solution of the organophosphate coumaphos (Chemservice #F2058) in ethanol was spread onto the surface each plate with a glass plate spreader. The plates were then placed in a laminar flow hood until the ethanol evaporated. Once the plates were dry, maize callus transformed with a maize expression vector containing the ubiquitin promoter, the BAASS (SEQ ID NO:2), the polynucleotide encoding an enzyme having organophosphate hydrolase activity (SEQ ID NO:1), and the pinII terminator ("transformed callus") was transferred to the surface of one plate, and callus that was not transformed with a polynucleotide encoding an enzyme having organophosphate hydrolase activity ("non-transformed callus") was transferred to the surface of the other plate. The plates were then sealed, and stored in a standard growth chamber.

At two days post-transfer, the plates were examined under ultraviolet light, and fluorescence, if any, was determined. Callus on the plate containing transformed callus fluoresced, while callus on the plate containing the non-transformed callus did not. Similar results were observed at six days post-transfer.

These results indicate that the organophosphate coumaphos is degraded/hydrolyzed by an enzyme having organophosphate hydrolase activity, that such degradation/hydrolysis can be detected, and that a polynucleotide encoding such an enzyme can be used as a screenable marker for transformation.

EXAMPLE 6

Use of Organophosphate Hydrolase as Selectable Marker in Non-Plants

Because organophosphates have insecticidal and fungicidal properties in addition to herbicidal properties, it will be appreciated by those of skill in the art that the cells used in the inventive methods are not limited to plant cells. Accordingly, a polynucleotide encoding an enzyme having organophosphate hydrolase activity can be obtained from, for example, *Flavobacterium* sp. (Genbank accession number M29593), and this sequence can be translated into a protein sequence and then back translated into a DNA sequence using, for example, an animal (i.e., insect) or fungal (i.e., yeast) codon usage table with the BACKTRANSLATE program of the GCG Wisconsin package (Wisconsin Package, version 9, Genetics Computer Group (GCG), Madison, Wis.). The sequence can then be searched for putative deleterious sequences using the FINDPATTERN program of the GCG Wisconsin package. Alternative codons can be chosen to eliminate the deleterious mRNA signals in the coding sequence and to add convenient enzyme restriction sites to facilitate downstream cloning. Codons that reflect less than 20% usage can be avoided. The completed sequence can be analyzed for unique restriction sites with the Vector NTI program. Five roughly equidistant sites can be chosen for the construction of the polynucleotide encoding the enzyme having organophosphate hydrolase activity. Oligonucleotides can be ordered in 50 bp lengths with 25 bp overhangs. These can be annealed and amplified by PCR. Amplified products can be trapped in a vector and transformed into competent cells. Colonies can be analyzed by restriction analysis and by DNA sequencing. Correct clones can be subcloned together in an appropriate vector. After the complete sequence is assembled, a suitable signal sequence can be added to ensure high expression in the particular animal or fungal cell that is ultimately to be transformed. The sequence can then be cloned into a suitable expression vector having appropriate regulatory elements, and the appropriate animal or fungal cells can be transformed using any of variety of techniques known in the art for transforming such cells.

Transformants can be selected for by contacting the cells with an organophosphate such that if the cells do not contain the polynucleotide encoding an enzyme having organophosphate hydrolase activity and such an enzyme is not thereby produced, the cell growth is inhibited.

EXAMPLE 7

Use of Organophosphate Hydrolase as Screenable Marker in Non-Plants

A polynucleotide encoding an enzyme having organophosphate hydrolase activity can be obtained from, for example, *Flavobacterium* sp. (Genbank accession number M29593), and this sequence can be translated into a protein sequence and then back translated into a DNA sequence using, for example, an animal (i.e., insect), bacterial (i.e., *E. coli*) or fungal (i.e., yeast) codon usage table with the BACKTRANSLATE program of the GCG Wisconsin package (Wisconsin Package, version 9, Genetics Computer Group (GCG), Madison, Wis.). The sequence can then be searched for putative deleterious sequences using the FINDPATTERN program of the GCG Wisconsin package. Alternative codons can be chosen to eliminate the deleterious mRNA signals in the coding sequence and to add convenient enzyme restriction sites to facilitate downstream cloning. Codons that reflect less than 20% usage can be avoided. The completed sequence can be analyzed for unique restriction sites with the Vector NTI program. Five roughly equidistant sites can be chosen for the construction of the polynucleotide encoding the enzyme having organophosphate hydrolase activity. Oligonucleotides can be ordered in 50 bp lengths with 25 bp overhangs. These can be annealed and amplified by PCR. Amplified products can be trapped in a vector and transformed into competent cells. Colonies can be analyzed by restriction analysis and by DNA sequencing. Correct clones can be subcloned together in an appropriate vector. After the complete sequence is assembled, a suitable signal sequence can be added to ensure high expression in the particular animal, bacterial, or fungal cell that is ultimately to be transformed. The sequence can then be cloned into a suitable expression vector having appropriate regulatory elements, and the appropriate animal, bacterial, or fungal cells can be transformed using any of variety of techniques known in the art for transforming such cells.

Transformants can be selected for by contacting the cells with an organophosphate such that if the cells contain the polynucleotide encoding an enzyme having organophosphate hydrolase activity and such an enzyme is thereby produced, the organophosphate is hydrolyzed. Such hydrolysis can be detected by suitable means.

EXAMPLE 8

Production of Enzyme Having Organophosphate Hydrolase Activity

An enzyme having organophosphate hydrolase activity that is produced by transformed cells containing a polynucleotide encoding an enzyme having organophosphate hydrolase activity is purified by standard methods known to those in the art.

PROSPECTIVE EXAMPLE 9

Use of Organophosphate Hydrolase as a Selectable Marker in Cell Cultures

This prospective example shows how to evaluate control cells for their ability to grow in the presence of organophosphates and to evaluate transgenic cultures for their ability to grow in the presence of a selected organophosphate.

Figure 6:
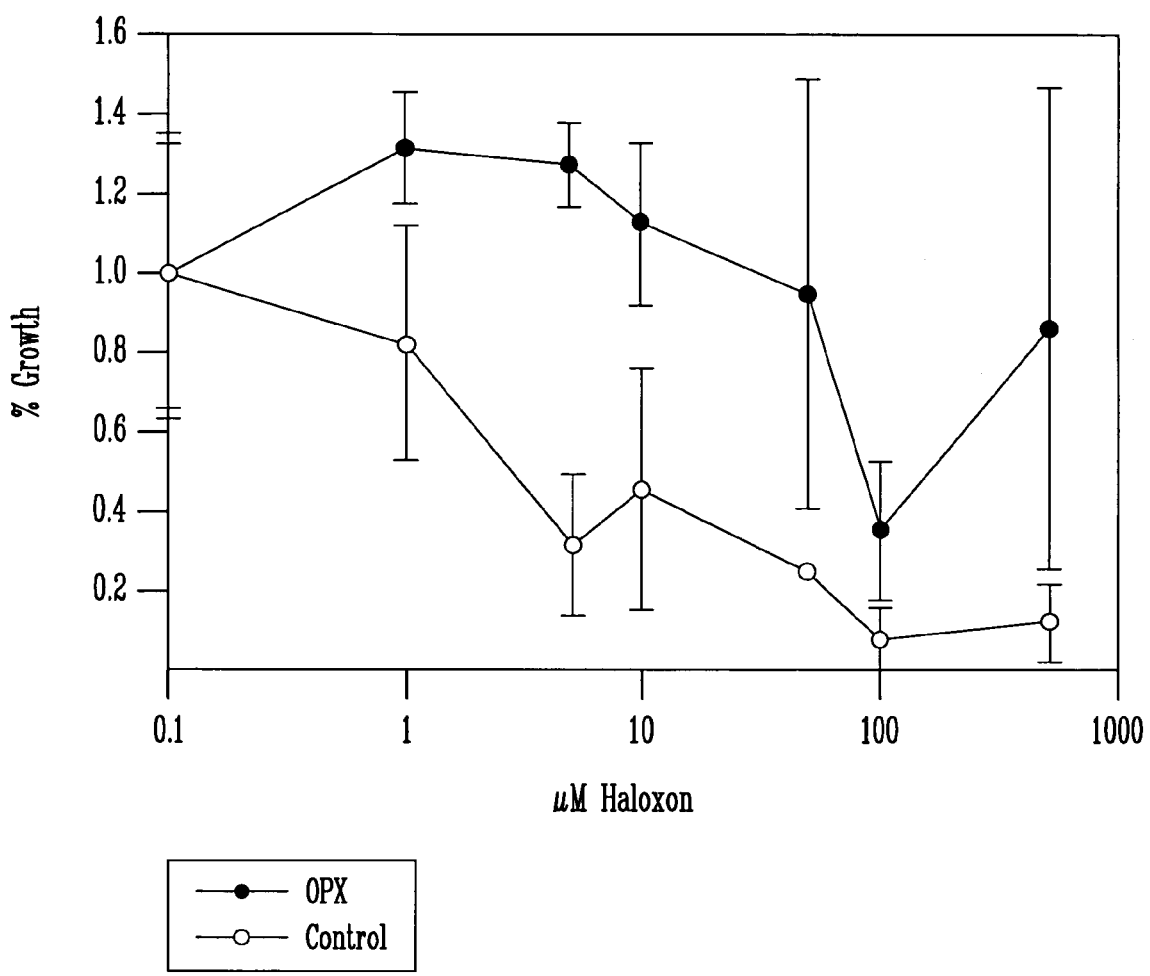
FIG. 6 is a haloxon graph showing the ability of transgenic organophosphate hydrolase (OPH) cells to grow at concentrations where control cultures would not.

A concentration is selected that allows for the cells to grow when organophosphate hydrolase (OPH) is expressed but not when it is absence in the cell cultures. By way of prospective example, haloxon can be made up in 100, 10 and 1 mg/ml stocks in DMSO. These stock solutions can be used to make plant tissue cultures plates with haloxon concentrations of 1, 5, 10, 50, 100, and 500 µM. Control plates contain a similar amount of DMSO compared to the haloxon plates. The tissue culture is a modified 5630 media without added bialaphos. Approximately 0.5 g of callus tissue is added to each plate. Exact tissue mass is calculated by pre-weighing the plate prior to the addition of callus and weighing the plate after the tissue has been added. The control cells are transformed with the OPH gene. Such transformation methods are well known in the art. Tissue is transferred to fresh media about every two weeks for six weeks and the tissue mass is calculated at every plate change. Then select for cells growing in the presence of the selected organophosphate and regenerate plants. The plants can then be verified as transgenic by a variety of methods, such as enzymatic active of OPH, PCR of the gene, scorable active of the OPH, or the presence of a second gene that was co-transformed with OPH. In order to compare both lines, results are reported as percentage growth compared to the control. The total growth of each line at each treatment is divided by the total growth of the control over the same period and multiplied by 100. This percentage is then graphed. Control results are graphed at 0.1 on the µM Haloxon axis due to the logarithmic scale. The haloxon graph as shown in FIG. 6 demonstrates the ability of the transgenic OPH cells to grow at concentrations where control cultures would not.

One of ordinary skill in the art, with the aid of the present disclosure, can affect various changes, substitutions of equivalents and other alterations to the methods and compositions herein set forth, in order to practice this invention. Therefore, the protection granted by letters patent should not be limited except by the language of the claims as set forth below.

We claim:

1. A method for determining whether a plant cell has incorporated and expresses a polynucleotide, the method comprising:
   introducing into the cell a construct comprising a polynucleotide encoding an enzyme having organophosphate hydrolase activity;
   contacting the cell or progeny of said cell with an organophosphate such that if the cell contains the construct and an enzyme having organophosphate hydrolase activity is thereby expressed, the enzyme having organophosphate hydrolase activity hydrolyzes the organophosphate; and
   detecting the hydrolysis such that extraction of the hydrolysis product from the cell is not necessary to detect the hydrolysis,
   thereby determining whether the cell has incorporated a polynucleotide under conditions that do not require destruction of the cell.

2. The method of claim 1, wherein the organophosphate is selected from the group consisting of acephate, azinophos-methyl, demeton-S-methyl, malathion, phosalone, amiprophos-methyl, bensulide, butamiphos, piperophos, paraoxon, DFP, coumaphos, soman, and VX.

3. The method of claim 1, wherein the organophosphate is amiprophos-methyl.

4. The method of claim 1, wherein the polynucleotide is SEQ ID NO:1.

5. The method of claim 1, wherein the plant cell is a maize plant cell.

6. The method of claim 1, wherein hydrolysis is detected by a method selected from the group consisting of visual observation of products produced by hydrolysis, fluorescence, phosphorescence and spectrophotometry.

7. The method of claim 1, wherein hydrolysis is detected by fluorescence.

8. The method of claim 1, wherein hydrolysis is detected by phosphorescence.

9. The method of claim 1, wherein hydrolysis results in a growth advantage of the cell compared to cells which do not have the construct.

10. A method for determining whether a plant cell has incorporated a first polynucleotide, the method comprising:

introducing into the cell a construct comprising a first polynucleotide and a second polynucleotide, wherein the second polynucleotide encodes an enzyme having organophosphate hydrolase activity;

contacting the cell or progeny of said cell with an organophosphate such that if the cell contains the construct and an enzyme having organophosphate hydrolase activity is thereby expressed, the enzyme having organophosphate hydrolase activity hydrolyzes the organophosphate; and detecting the hydrolysis such that extraction of the enzyme from the cell is not necessary to detect the hydrolysis, thereby determining whether the cell has incorporated a first polynucleotide under conditions that do not require destruction of the cell.

11. The method of claim 10, wherein the organophosphate is selected from the group consisting of acephate, azinophos-methyl, demeton-S-methyl, malathion, phosalone, amiprophos-methyl, bensulide, butamiphos, piperophos, paraoxon, DFP, coumaphos, soman, and VX.

12. The method of claim 10, wherein the organophosphate is amiprophos-methyl.

13. The method of claim 10, wherein the second polynucleotide is SEQ ID NO:1.

14. The method of claim 10, wherein the plant cell is a maize plant cell.

* * * * *